US009869663B2

(12) United States Patent
Tsuzuki et al.

(10) Patent No.: US 9,869,663 B2
(45) Date of Patent: Jan. 16, 2018

(54) GAS SENSOR APPARATUS AND CONCENTRATION MEASUREMENT METHOD PERFORMED THROUGH USE OF GAS SENSOR

(71) Applicant: NGK SPARK PLUG CO., LTD., Nagoya-shi, Aichi (JP)

(72) Inventors: Masao Tsuzuki, Kakamigahara (JP); Toyohiro Tsukahara, Ichinomiya (JP)

(73) Assignee: NGK SPARK PLUG CO., LTD., Aichi (JP)

( * ) Notice: Subject to any disclaimer, the term of this patent is extended or adjusted under 35 U.S.C. 154(b) by 62 days.

(21) Appl. No.: 14/851,793

(22) Filed: Sep. 11, 2015

(65) Prior Publication Data

US 2016/0077072 A1 Mar. 17, 2016

(30) Foreign Application Priority Data

Sep. 16, 2014 (JP) .................................. 2014-187834

(51) Int. Cl.
*G01N 33/00* (2006.01)
*G01M 15/10* (2006.01)

(52) U.S. Cl.
CPC ....... *G01N 33/0006* (2013.01); *G01M 15/104* (2013.01); *G01M 15/106* (2013.01); *G01N 33/0016* (2013.01)

(58) Field of Classification Search
CPC .......... G01N 33/0016; G01N 33/0006; G01M 15/104; G01M 15/106
See application file for complete search history.

(56) References Cited

U.S. PATENT DOCUMENTS

| | | | | |
|---|---|---|---|---|
| 2002/0139360 | A1* | 10/2002 | Sato | F02D 41/0037 123/698 |
| 2008/0237064 | A1* | 10/2008 | Nakasone | G01N 27/4175 205/781 |
| 2009/0223820 | A1* | 9/2009 | Ishiguro | G01N 27/419 204/424 |
| 2011/0036075 | A1* | 2/2011 | Hagiwara | F02D 35/026 60/285 |
| 2013/0036792 | A1 | 2/2013 | Tsuduki et al. | |
| 2014/0076741 | A1 | 3/2014 | Adams | |

FOREIGN PATENT DOCUMENTS

| | | |
|---|---|---|
| JP | 2001-173521 A | 6/2001 |
| JP | 2002-277434 A | 9/2002 |
| JP | 2013-36852 A | 2/2013 |
| JP | 10-176577 A | 6/2017 |

OTHER PUBLICATIONS

Office communication dated Nov. 13, 2017 in counterpart Japanese Patent Application No. 2014-187834, 6 pages total.

* cited by examiner

*Primary Examiner* — R. A. Smith
*Assistant Examiner* — John M Royston
(74) *Attorney, Agent, or Firm* — Sughrue Mion, PLLC

(57) ABSTRACT

A gas sensor apparatus including a gas sensor (10) which outputs an output value corresponding to the concentration of a specific gas component, and a computation section (30) which calculates a specific component concentration based on the output value output and a pressure value representing the pressure of the gas. The computation section (30) includes pressure change rate calculation means (31), pressure change rate judgment means (32), correction amount calculation means (33), and output correction means (34). Also disclosed is a concentration measurement method using the gas sensor.

5 Claims, 10 Drawing Sheets

GAS SENSOR APPARATUS AND CONCENTRATION MEASUREMENT METHOD PERFORMED THROUGH USE OF GAS SENSOR

BACKGROUND OF THE INVENTION

1. Field of the Invention

The present invention relates to a gas sensor apparatus and to a concentration measurement method using the gas sensor.

2. Description of the Related Art

In an internal combustion engine such as a diesel engine or a gasoline engine, an EGR control for returning exhaust gas to the intake gas side is generally performed so as to reduce fuel consumption and purify exhaust gas. In order to perform the EGR control, a gas sensor is used to measure the proportion of a specific gas component (e.g., oxygen) contained in the intake gas or the proportion of the specific gas component contained in the exhaust gas.

The gas sensor includes a sensor element disposed in a gas (i.e., a target for measurement). The sensor element outputs a value representing the concentration of a specific gas component (e.g., oxygen concentration), which is the ratio of the specific gas component. However, the value output from the sensor element is known to be affected not only by the concentration of the specific gas component of the gas but also the pressure of the gas.

In recent years, since the degree of fineness of control of an internal combustion engine has increased, there has been an increasing need for measuring the concentration of a specific gas component more accurately. In order to measure the concentration of a specific gas component of a gas (i.e., a target for measurement) more accurately, various methods have been proposed for eliminating the influence of the gas pressure upon the value output from the gas sensor (see, for example, Patent Document 1).

Patent Document 1 discloses a configuration including a sensor element which measures the concentration of a specific gas component of a gas (i.e., a target for measurement) and a pressure sensor which measures the pressure of the gas. In addition, Patent Document 1 proposes a method (correction method) for eliminating the influence of the gas pressure on the value which is output from the gas sensor and which represents the concentration of the specific gas component. In this method, the value output from the gas sensor is multiplied by a coefficient based on the pressure measured by the pressure sensor, whereby the influence of the gas pressure on the output value is eliminated.

[Patent Document 1] Japanese Patent Application Laid-Open (kokai) No. 2013-036852

3. Problems to be Solved by the Invention

The method described in the above-described Patent Document 1 gives rise to the following problem. In the case where a change in pressure with time is relatively small (in the case of a static pressure change), the influence of pressure on the value output from the gas sensor can be eliminated easily. However, in the case where a change in pressure with time is relatively large (in the case of a dynamic pressure change), the influence of pressure on the value output from the gas sensor cannot be completely eliminated, and the accuracy in measuring the concentration of the specific gas component is greatly deteriorated.

SUMMARY OF THE INVENTION

The present invention has been made to solve the above-described problems, and an object thereof is to provide a gas sensor apparatus and a concentration measurement method using the gas sensor which can suppress deterioration in measurement accuracy even when subjected to a dynamic pressure change.

The above-described object has been achieved by providing, in a first aspect (1), a gas sensor apparatus comprising: a gas sensor which outputs an output value corresponding to the concentration of a specific gas component contained in a gas flowing through a flow passage provided in an internal combustion engine; and a computation section which calculates a specific component concentration based on the output value output from the gas sensor and a pressure value representing the pressure of the gas. The computation section comprises means for calculating a pressure change rate from a change in pressure per a predetermined time period; means for judging whether or not the pressure change rate exceeds a predetermined rate; means for calculating a correction amount for the output value based on the calculated pressure change rate when the pressure change rate is judged to have exceeded the predetermined rate; and means for correcting the output value from the gas sensor using the correction amount calculated by the correction amount calculation means.

In a second aspect (2), the present invention provides a concentration measurement method performed using a gas sensor which outputs an output value corresponding to the concentration of a specific gas component contained in a gas flowing through a flow passage provided in an internal combustion engine, the method being adapted to calculate a specific component concentration based on the output value output from the gas sensor and a pressure value representing the pressure of the gas. The method comprises calculating a pressure change rate from a change amount of the pressure value per a predetermined time period; judging whether or not the pressure change rate exceeds a predetermined rate; calculating a correction amount for the output value based on the calculated pressure change rate when the pressure change rate is judged to have exceeded the predetermined rate; and correcting the output value from the gas sensor using the calculated correction amount.

According to the gas sensor apparatus (1) of the present invention and the concentration measurement method (2) performed using a gas sensor according to the present invention, when the pressure change rate exceeds the predetermined rate, the output value of the oxygen sensor is corrected using a correction amount calculated based on the pressure change rate. In other words, in the case where the pressure changes dynamically, the output value of the oxygen sensor is corrected using a correction amount corresponding to the degree of the dynamic change. Therefore, deterioration in measurement accuracy of the specific component concentration can be suppressed even when the pressure changes dynamically.

Meanwhile, when the pressure change rate is equal to or less than the predetermined rate, the correction of the output value of the oxygen sensor performed using the correction amount calculated based on the pressure change rate is not performed. For example, in the case of a dynamic pressure change, such as the case where the pressure changes at a relatively high frequency, correction of the output value of the oxygen sensor is performed; and in the case of a static pressure change, such as the case where the pressure changes at a relatively low frequency, correction of the output value of the oxygen sensor is not performed. Therefore, deterioration in measurement accuracy can be suppressed even when the pressure changes dynamically.

In a preferred embodiment (3), the above-described gas sensor apparatus (1) further comprises means for calculating a change amount of the pressure value per the predetermined time period, and means for judging whether or not the change amount of the pressure value exceeds a predetermined change amount; and the correction amount calculation means calculates the correction amount for the output value based on the calculated pressure change rate when the pressure change rate judgment means judges that the pressure change rate has exceeded the predetermined rate and the pressure change amount judgment means judges that the change amount of the pressure value has exceeded the predetermined change amount.

In a preferred embodiment (4), the above-described concentration measurement method (2) further comprises calculating a change amount of the pressure value per the predetermined time period; and judging whether or not the change amount of the pressure value exceeds a predetermined change amount, wherein the correction amount calculation step calculates the correction amount for the output value based on the calculated pressure change rate when the pressure change rate is judged to have exceeded the predetermined rate and the change amount of the pressure value is judged to have exceeded the predetermined change amount.

As a result of the output value of the oxygen sensor being corrected using a correction amount when the pressure value change amount exceeds the predetermined change amount as described above, it is possible to suppress deterioration in measurement accuracy of the specific component concentration. For example, in the case of a static pressure change, such as the case where the pressure value change amount per the predetermined time period is equal to or less than the predetermined change amount, the correction of the output value of the oxygen sensor is not performed; and in the case of a dynamic pressure change, such as the case where the pressure value change amount per the predetermined time period exceeds the predetermined change amount, the correction of the output value of the oxygen sensor is performed. Therefore, deterioration in measurement accuracy can be suppressed even when the pressure changes dynamically.

In yet another preferred embodiment (5), the above-described gas sensor apparatus (1) or (3) further comprises a pressure sensor which measures the pressure of the gas and outputs a pressure raw value representing the measured pressure and averaging means for averaging the pressure raw value, wherein a value output from the averaging means is used as the pressure value. As a result of the averaged pressure raw value being used as the pressure value, deterioration in the measured accuracy of the specific component concentration can be further suppressed.

Effects of the Invention

According to the gas sensor apparatus of the present invention and the concentration measurement method performed using a gas sensor of the present invention, when the pressure change rate exceeds the predetermined rate, the output value of the gas sensor is corrected using a correction amount calculated based on the pressure change rate. In other words, in the case where the pressure changes dynamically, the output value of the gas sensor is corrected using a correction amount corresponding to the degree of dynamic change. Therefore, the apparatus and method of the present invention can suppress deterioration in the measurement accuracy of the specific component concentration even when the pressure changes dynamically.

DESCRIPTION OF REFERENCE NUMERALS

Figure 1:
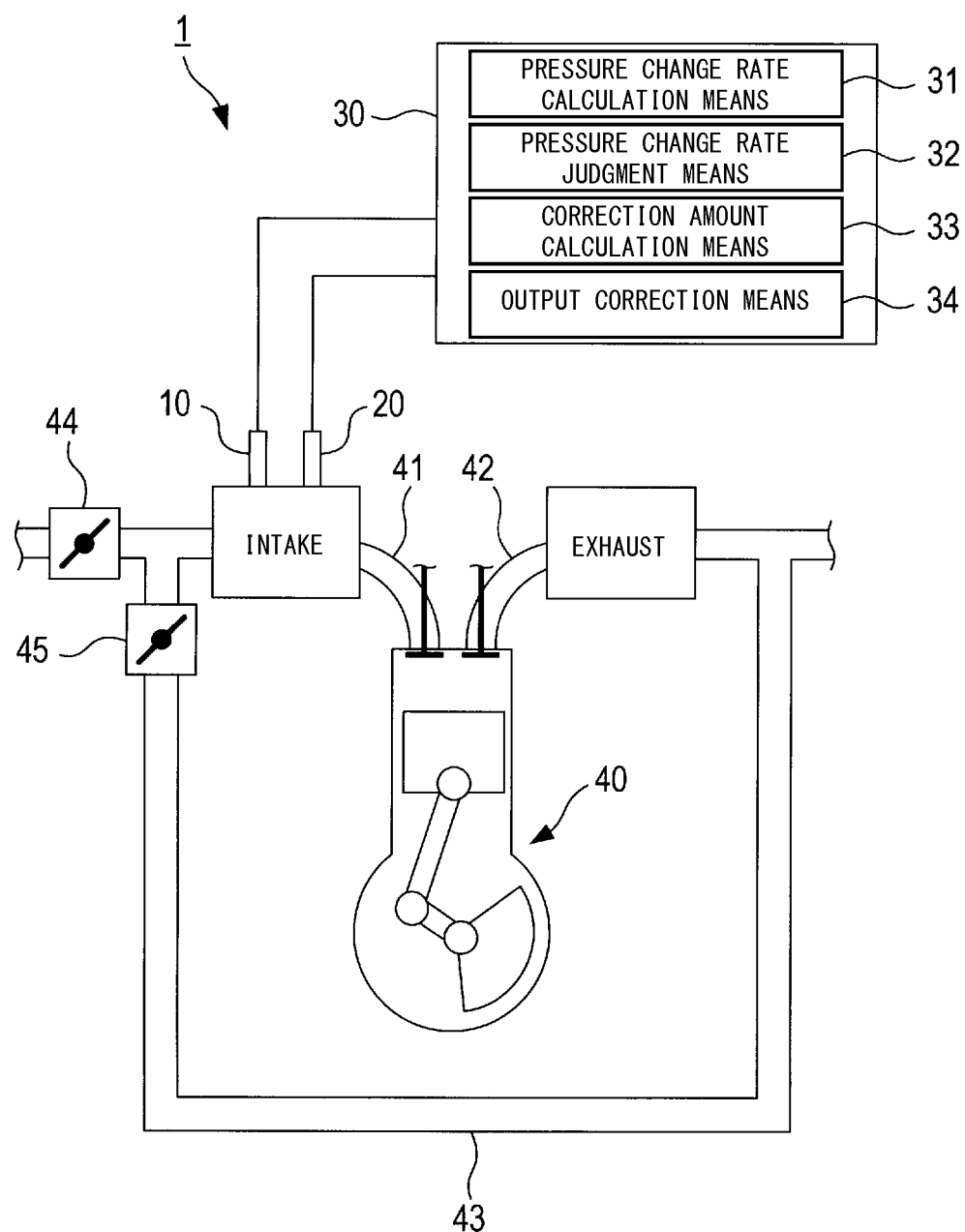
FIG. 1 is a schematic diagram of the configuration of a gas sensor apparatus according to a first embodiment of the present invention.

Reference numerals used to identify various features in the drawings include the following:
1: gas sensor apparatus, 10: oxygen sensor (gas sensor), 20: pressure sensor, 30: engine control unit (computation section), 31: pressure change rate calculation means, 32: pressure change rate judgment means, 33: correction amount calculation means, 34: output correction means, 36: change amount calculation means, 37: pressure change amount judgment means, 38: averaging means, 40: internal combustion engine, S30: pressure change rate calculation step, S40: pressure change rate judgment step, S41: change amount calculation step, S42: change amount judgment step, S50: correction amount calculation step, and S60: output correction step

DETAILED DESCRIPTION OF THE PREFERRED EMBODIMENTS

The present invention will next be described in detail with reference to the drawings. However, the present invention should not be construed as being limited thereto.

First Embodiment

A gas sensor apparatus 1 according to a first embodiment of the present invention will now be described with reference to FIG. 1 to FIG. 8. FIG. 1 is a schematic diagram showing the configuration of the gas sensor apparatus 1 according to the present embodiment.

As shown in FIG. 1, the gas sensor apparatus 1 measures the concentration of oxygen contained in the intake gas which is taken into an internal combustion engine 40. The oxygen concentration measured by the gas sensor apparatus 1 is used to control the internal combustion engine 40; for example, it is used to control the air-fuel ratio. The oxygen concentration can also be used to calculate an EGR ratio which is the ratio between the oxygen concentration when exhaust gas is circulated to the intake side and the oxygen concentration when exhaust gas is not circulated to the intake side. The gas sensor apparatus 1 is mainly composed of an oxygen sensor (gas sensor) 10, a pressure sensor 20, and an engine control unit (computation section) 30 (hereinafter referred to as an "ECU 30").

Notably, in the present embodiment, the gas sensor apparatus 1 of the present invention is used to measure the concentration of oxygen contained in the intake gas which is taken into the internal combustion engine 40; however, the gas sensor apparatus 1 of the present invention may be used to measure the concentration of oxygen contained in exhaust gas which is discharged from the internal combustion engine 40. That is, no particular limitation is imposed on the gas for which oxygen concentration is measured. However, use of the gas sensor apparatus of the present invention is effective for measuring the concentration of oxygen contained in intake gas. This is because the pressure of the intake gas changes greatly, and the $O_2$ concentration and the output value of a sensor element, which will be described below, are more likely to incur measurement errors.

The oxygen sensor 10 and the pressure sensor 20 are disposed in an intake pipe 41 of the internal combustion engine 40. Specifically, the oxygen sensor 10 and the pressure sensor 20 are disposed on the internal combustion engine 40 side in relation to a junction point where the intake pipe 41 and an exhaust gas recirculation pipe 43 (hereinafter referred to as an "EGR pipe 43") are connected together. Namely, these sensors are disposed downstream of the junction point. Meanwhile, an intake valve 44 for controlling the flow rate of air flowing through the intake pipe 41 is disposed in the intake passage 41 at a position upstream of the positions at which the oxygen sensor 10 and the pressure sensor 20 are disposed. Notably, no particular limitation is imposed on the relative positions of the oxygen sensor 10 and the pressure sensor 20. That is, the oxygen sensor 10 may be disposed upstream of the pressure sensor 20, or the pressure sensor 20 may be disposed upstream of the oxygen sensor 10.

Notably, the EGR pipe 43 connects an exhaust pipe 42 and the intake pipe 41 so as to lead a portion of the exhaust gas flowing through the exhaust pipe 42 to the intake pipe 41. Namely, the EGR pipe 43 is provided to recirculate the exhaust gas. The EGR pipe 43 has a control valve 45 for controlling the recirculation amount of the exhaust gas.

The oxygen sensor 10 measures the concentration of oxygen contained in the intake gas flowing through the intake pipe 41, and outputs a current Ip which is an output value representing the oxygen concentration. The value of the current Ip changes with the concentration of oxygen contained in the intake gas as well as the pressure of the intake gas flowing through the intake pipe 41. In other words, the current Ip is a function of the oxygen concentration, and is also a function of the pressure of the intake gas. Notably, no particular limitation is imposed on the type, etc., of the oxygen sensor 10, so long as it is a commonly-known sensor having the above-described characteristic.

The pressure sensor 20 measures the pressure of the intake gas flowing through the intake pipe 41 so as to output a measurement signal corresponding to the pressure of the intake gas. Notably, a commonly-known pressure sensor may be used as the pressure sensor 20. That is, no particular limitation is imposed on the type, etc., of the pressure sensor 20.

The ECU 30 obtains, through computation, the oxygen concentration of the intake gas flowing through the intake pipe 41 based on the output value from the oxygen sensor 10 and the pressure measured by the pressure sensor 20. The ECU 30 controls at least the operation state of the internal combustion engine 40 based on the obtained oxygen concentration.

The ECU 30 is a computer system which includes a CPU (central processing unit), a ROM, a RAM, a hard disk drive, an input output interface, etc. Control programs stored in the ROM, etc., cause the CPU, the RAM, etc., to function at least as pressure change rate calculation means 31, pressure change rate judgment means 32, correction amount calculation means 33, and output correction means 34. Notably, an oxygen concentration calculation method in the ECU 30; specifically, the details of computations in the pressure change calculation means 31, the pressure change rate judgment means 32, the correction amount calculation means 33, and the output correction means 34 will be described below.

Figure 2:
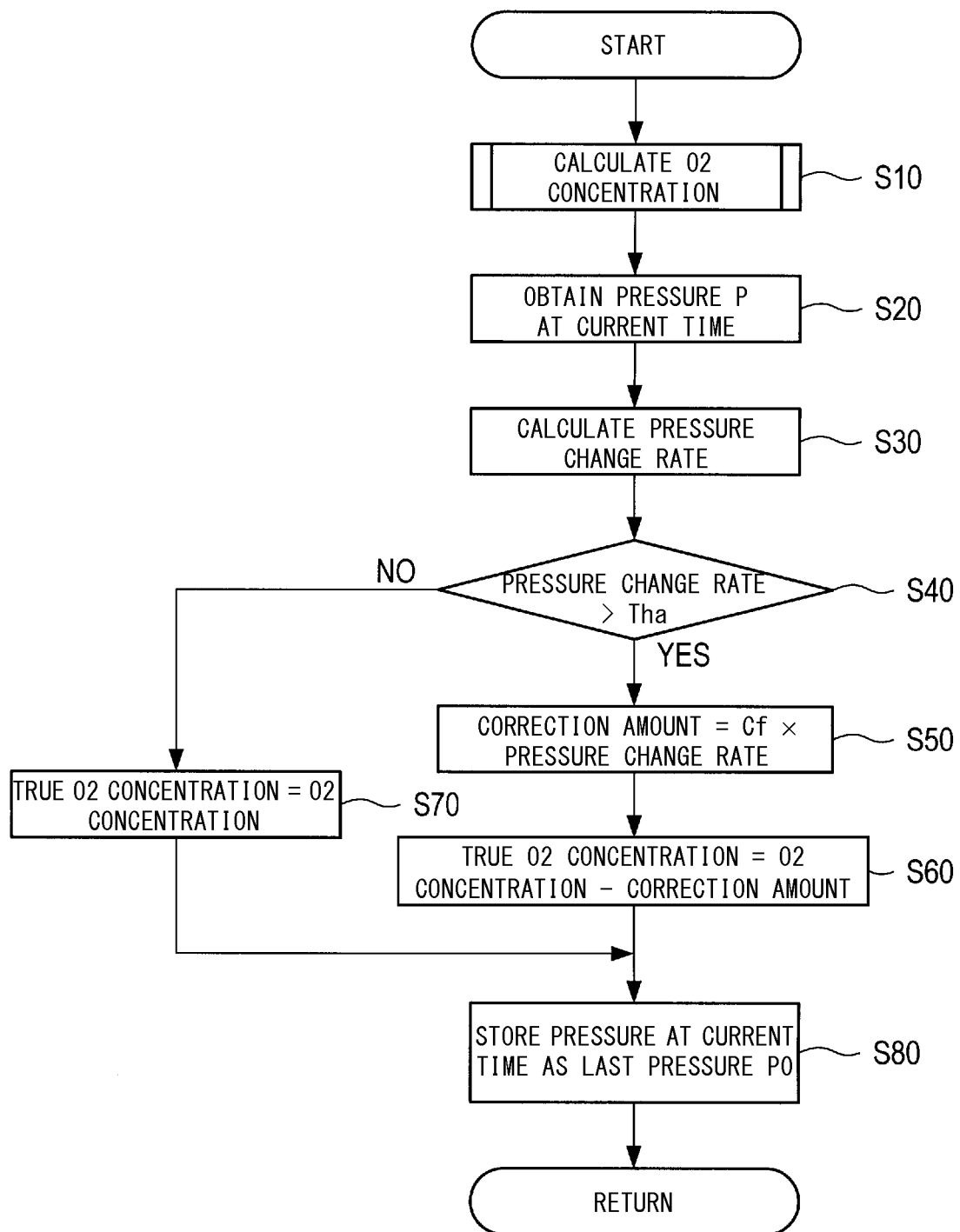
FIG. 2 is a flowchart describing an oxygen concentration correction method performed by the ECU shown in FIG. 1.
Figure 3:
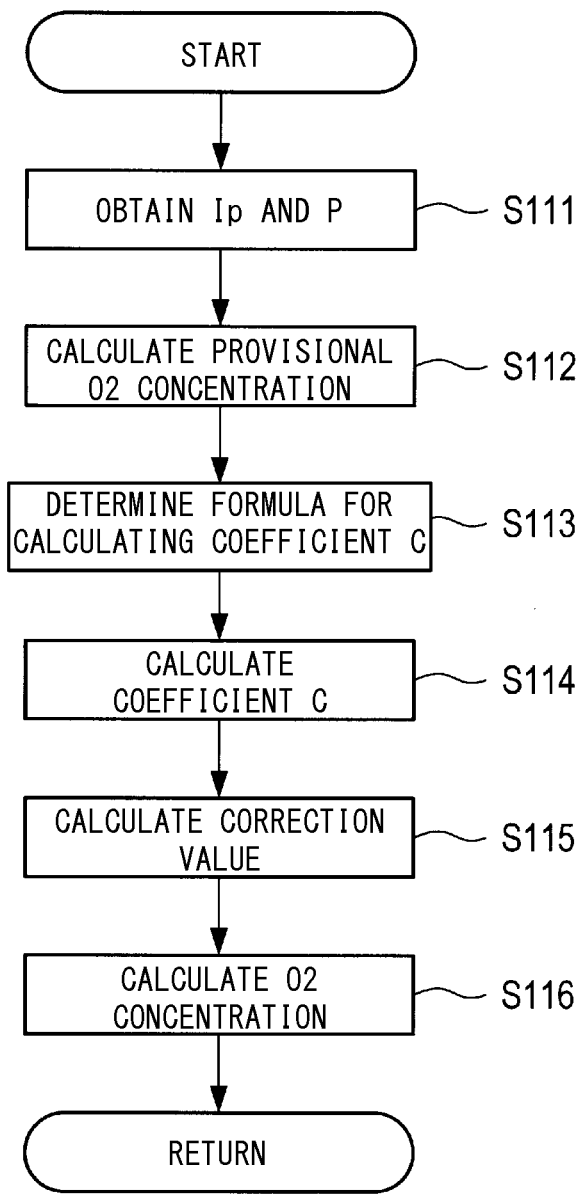
FIG. 3 is a flowchart describing an oxygen concentration calculation method performed by the ECU shown in FIG. 1.

Next, the oxygen concentration calculation method in the gas sensor apparatus 1 having the above-described configuration will be described. FIGS. 2 and 3 are flowcharts describing the oxygen concentration calculation method performed by the ECU 30 shown in FIG. 1. Notably, in the present embodiment, the calculation of oxygen concentration in the gas sensor apparatus 1 is repeatedly performed at arbitrary intervals.

When the oxygen concentration calculation processing in the gas sensor apparatus 1 is started, as shown in FIG. 2, the ECU 30 starts the calculation of oxygen concentration (S10). Specifically, as shown in FIG. 3, the ECU 30 executes processing of obtaining an output value (current Ip) output from the oxygen sensor 10 and a pressure-related electrical signal which is a measurement signal output from the pressure sensor 20 (S111). On the basis of a previously stored table or the like, the ECU 30 converts the pressure-related electrical signal to a pressure value P representing the pressure of the intake gas flowing inside the intake pipe 41.

Next, the ECU 30 executes processing of calculating a provisional $O_2$ concentration (corresponding to a "provisional specific component concentration" of the invention) in accordance with Expression (1) given below (S112). The provisional $O_2$ concentration is a value which represents the oxygen concentration and which can be obtained by substituting the value of the current Ip and the pressure value P (representing the pressure of the intake gas) into Expression (1) derived from Fick's law.

$$\text{Provisional } O_2 \text{ concentration} = 1 - e^{\left(-A \cdot Ip \cdot \frac{B+P}{P}\right)} \quad (1)$$

In Expression (1), Ip is the output value from the oxygen sensor 10, and P is the pressure value representing the pressure measured by the pressure sensor 20. Notably, A and B are constants determined such that two provisional specific component concentrations computed for two pressure values approximate each other. Specifically, A is a constant determined by Expression (2) given below, and B is a constant determined by Expression (3) given below.

$$A = \frac{LR}{4SFKKT^{0.75}} \quad (2)$$

$$B = \frac{k}{k}T^{1.25} \quad (3)$$

In Expressions (2) and (3), L is the length (m) of a diffusion hole of the oxygen sensor 10; R is the gas constant (8.314 $JK^{-1}$ $mol^{-1}$); S is the cross-sectional area ($m^2$) of the diffusion hole of the oxygen sensor 10; F is the Faraday constant (9.6485×$10^4$ $Cmol^{-1}$); and T is the temperature (K) of the gas passing through the diffusion hole of the oxygen sensor 10.

Notably, no particular limitation is imposed on the method of obtaining the above-described coefficients A and B. That is, the above-described coefficients A and B may be respectively calculated from the above-described Expressions (2) and (3), or they may be empirically obtained by measuring the oxygen concentration of a gas whose $O_2$ concentration and pressure are known.

Once the provisional $O_2$ concentration is calculated, the ECU 30 then executes processing of determining a calculation formula for calculating a coefficient C (S113). The coefficient C corresponding to a coefficient contained in the correction term of the following Equation (4) for obtaining an $O_2$ concentration (corresponding to a "specific component concentration" of the invention) from the provisional $O_2$ concentration (see Expression (5)).

$O_2$ concentration=provisional $O_2$ concentration−correction term (4)

$$\text{Correction } termn = \text{provisional } O_2 \text{ concentration} \cdot \frac{C}{100} \quad (5)$$

The coefficient C is calculated in accordance with different calculation formulas depending on the pressure of the intake gas measured by the pressure sensor 20. In the present embodiment, when the pressure of the intake gas is lower than a predetermined pressure value $P_T$, the following Expression (6) is selected as a calculation formula, and when the pressure of the intake gas is equal to or higher than the predetermined pressure value $P_T$, the following Expression (7) is selected as a calculation formula.

$C=ax^2+bx+c$ (6)

$C=dx+e$ (7)

Figure 4A:
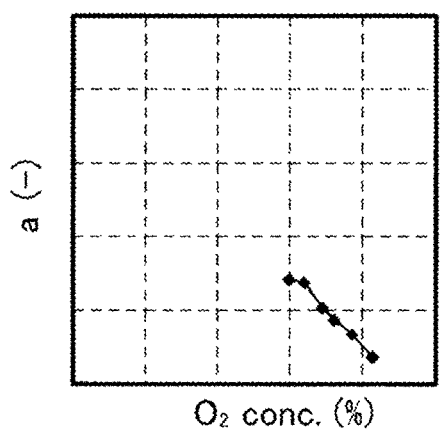
FIGS. 4A to 4C are graphs showing the coefficients a, b, and c of a calculation formula for computing the coefficient C of a correction term.
Figure 4B:
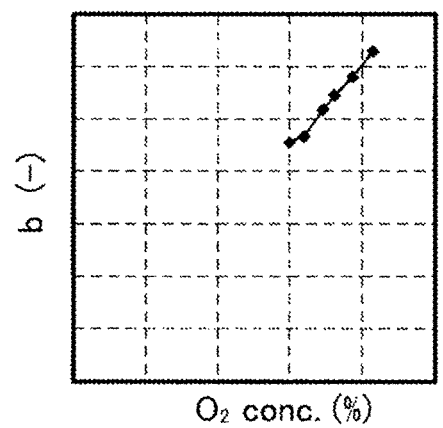
Figure 4C:
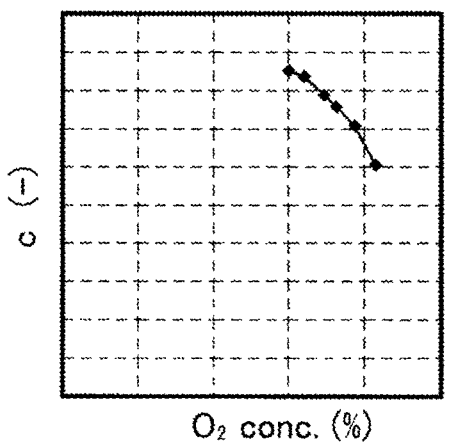
Figure 5A:
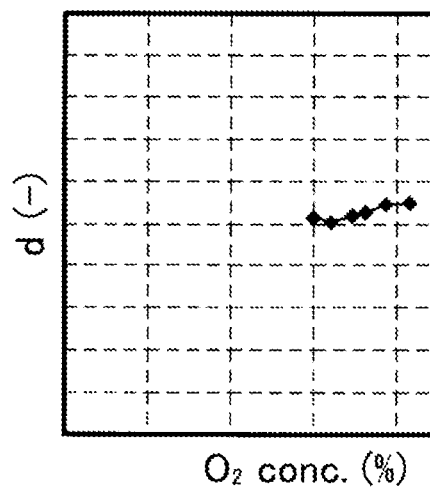
FIGS. 5A and 5B are graphs showing the coefficients d and e of another calculation formula for computing the coefficient C of the correction term.
Figure 5B:
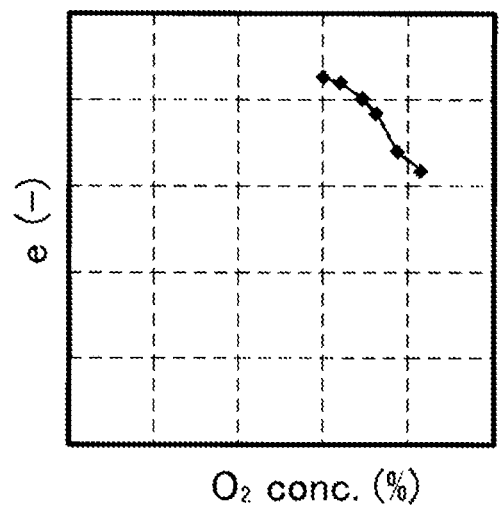

In Expressions (6) and (7), x is the intake gas pressure measured by the pressure sensor 20.

a is a coefficient determined based on the value of the provisional $O_2$ concentration. Specifically, as shown in FIG. 4A, a is a coefficient that decreases as the value of the provisional $O_2$ concentration increases. b is a coefficient determined based on the value of the provisional $O_2$ concentration. Specifically, as shown in FIG. 4B, b is a coefficient that increases with the value of the provisional $O_2$ concentration. c is a coefficient determined based on the provisional $O_2$ concentration. Specifically, as shown in FIG. 4C, c is a coefficient that decreases as the value of the provisional $O_2$ concentration increases.

d is a coefficient determined based on the value of the provisional $O_2$ concentration. Specifically, as shown in FIG. 5A, d is a coefficient that changes with the value of the provisional $O_2$ concentration. e is a coefficient determined based on the value of the provisional $O_2$ concentration. Specifically, as shown in FIG. 5B, e is a coefficient that decreases as the value of the provisional $O_2$ concentration increases.

After the calculation formula for computing the coefficient C is selected by the calculation means 31, processing of calculating the coefficient C is executed by the calculation means 31 (S114).

For example, when the intake gas pressure measured by the pressure sensor 20 is lower than the pressure value $P_T$, the calculation means 31 selects the above-described Expression (6) as a calculation formula, and computes the value of the coefficient C based on the values of the coefficients a, b, and c which correspond to the calculated provisional $O_2$ concentration and the intake gas pressure measured by the pressure sensor 20.

After having calculated the value of the coefficient C, the calculation means 31 executes processing of computing a correction value which is the value of the correction term (S115). Specifically, the calculation means 31 computes the value of the correction term based on the above-described Expression (5), the calculated provisional $O_2$ concentration, and the value of the coefficient C calculated in S114.

Subsequently, the calculation means 31 executes processing of calculating an $O_2$ concentration (specific component concentration) based on the above-described Expression (4), the calculated provisional $O_2$ concentration, and the value of the correction term calculated in S115 (S116).

When the $O_2$ concentration calculation processing at the ECU 30 ends, the ECU 30 returns to the routine of FIG. 2 and executes processing of obtaining the pressure value P at the current time (S20). The pressure value P may be obtained by obtaining the pressure-related electrical signal output from the pressure sensor 20 at the timing at which the processing of S20 is performed and converting the pressure-related electrical signal to the pressure value P based on a previously stored table or the like, or by storing the pressure value P obtained in, for example, the above-described S111 in the RAM of the ECU 30 or the like and reading the stored pressure value P.

Next, the pressure change rate calculation means 31 of the ECU 30 performs calculation processing of obtaining a pressure change rate (S30: a pressure change rate calculation step). The pressure change rate can be calculated by, for example, the following method. First, a last pressure value P0 obtained when a last $O_2$ concentration was calculated is read from the RAM of the ECU 30 or the like, and a pressure difference (which is the difference between the last pressure value P0 and the current pressure value P obtained at S20) is obtained. This pressure difference is divided by the time difference (predetermined period) between the current timing at which the last $O_2$ concentration was calculated and the timing at which the $O_2$ concentration is calculated, whereby the pressure change rate is obtained. Notably, the calculation method for obtaining the pressure change rate is not limited to the above-described method, and various other methods may be used.

When the pressure change rate is obtained, the pressure change rate judgment means 32 performs processing of comparing the obtained pressure change rate with a threshold Tha (a predetermined rate) for the pressure change rate so as to judge whether or not the obtained pressure change rate exceeds the threshold Tha (S40: a pressure change rate judgment step).

In the case where the pressure change rate is judged to have exceeded the threshold Tha (in the case of YES), the correction amount calculation means 33 performs computation processing of obtaining a correction amount (S50: a correction amount calculation step). The correction amount is used for correcting the $O_2$ concentration obtained in S10. Since the error contained in the $O_2$ concentration obtained in S10 correlates with the pressure change rate, the correction amount can be calculated by, for example, a method of multiplying the pressure change rate by a correction coefficient Cf.

When the correction amount is obtained, the output correction means 34 perform computation processing of obtaining an actual $O_2$ concentration (S60: an output correction step). The actual $O_2$ concentration is obtained by subtracting the correction amount obtained in S50 from the $O_2$ concentration obtained in S10. As a result, it is possible to obtain a more accurate $O_2$ concentration which has been corrected for the error which is contained in the $O_2$ concentration obtained in S10 and which depends on the dynamic pressure.

Meanwhile, in the case where the pressure change rate is judged by the processing of S40 that the pressure change rate is equal to or lower than the threshold Tha (in the case of NO), the output correction means 34 performs processing of regarding the $O_2$ concentration obtained in S10 as the actual $O_2$ concentration (S70). Namely, in the case where the $O_2$ concentration obtained in S10 does not contain an error depending on the dynamic pressure or in the case where the $O_2$ concentration obtained in S10 contains such an error but its influence is small, the $O_2$ concentration obtained in S10 is used as the actual $O_2$ concentration without correction.

When a more accurate $O_2$ concentration is obtained using the above-described correction, the output correction means 34 performs processing of storing the pressure value P used to calculate the $O_2$ concentration as the pressure value P0 obtained when the $O_2$ concentration was last calculated (S80). After that, the ECU 30 returns to S10 and repeatedly performs the above-described computation processing.

Figure 6:
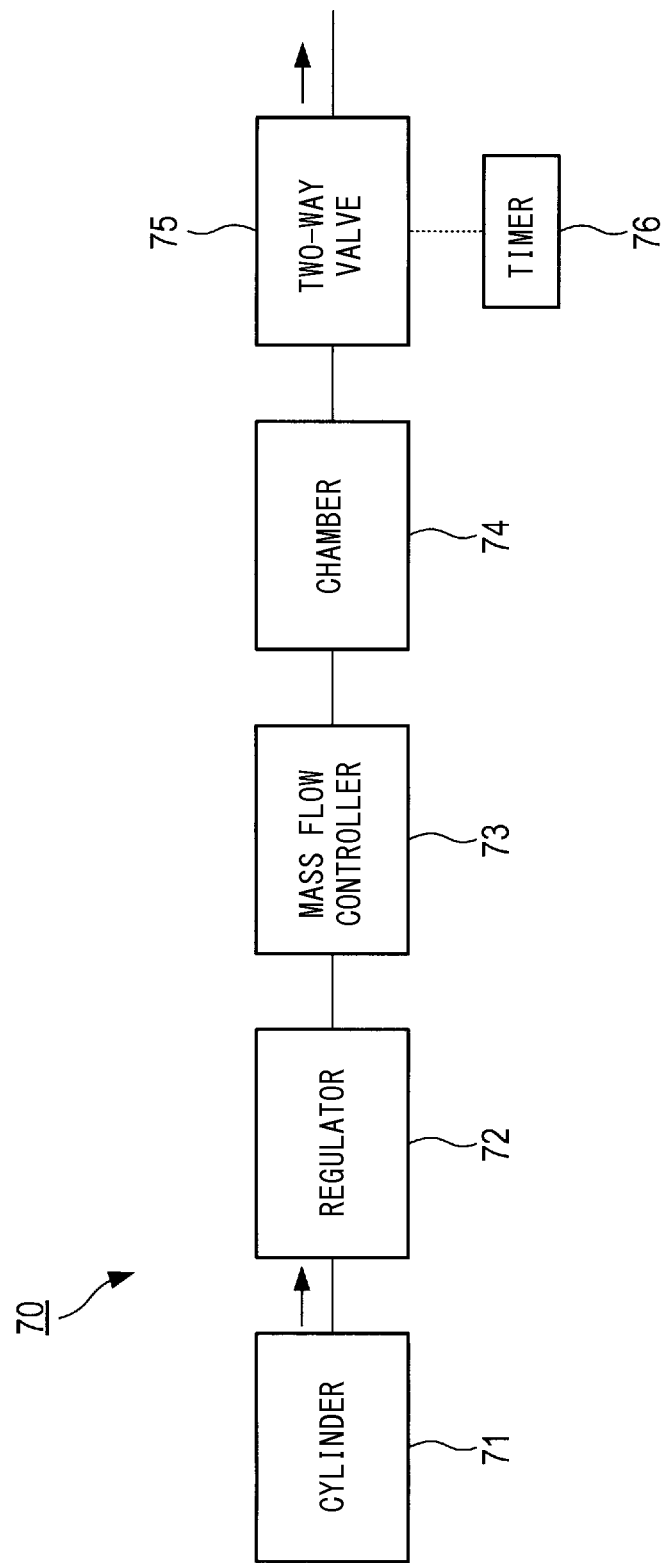
FIG. 6 is a schematic diagram showing the overall configuration of an experimental apparatus for the gas sensor apparatus.

Next, the results of an experiment in which oxygen concentration was measured using the gas sensor apparatus 1 having the above-described configuration will be described with reference to FIGS. 6 to 8. An experiment for measuring oxygen concentration using the gas sensor apparatus 1 is performed using an experimental apparatus 70 shown in FIG. 6.

The experimental apparatus 70 is mainly composed of a cylinder 71 in which a gas containing oxygen at a predetermined concentration is stored; a regulator 72 which adjusts the pressure of the gas supplied from the cylinder 71; a mass flow controller 73 which adjusts the flow rate of the gas; a chamber 74 to which the gas sensor apparatus 1 is attached; and a two-way valve 75 connected to a timer 76.

Figure 7:
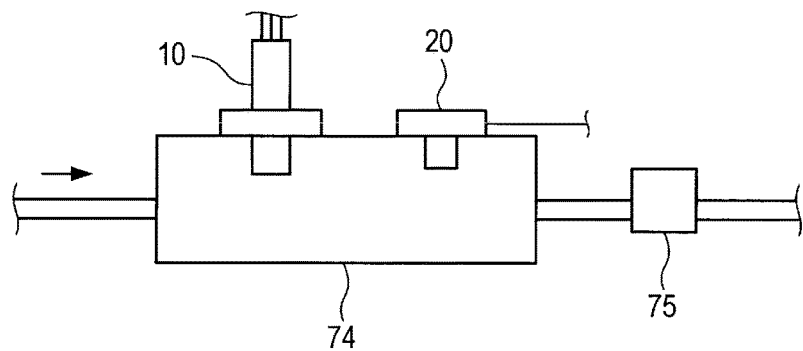
FIG. 7 is a schematic view showing the configuration of the chamber of FIG. 6.

As shown in FIG. 7, the oxygen sensor 10 and the pressure sensor 20 of the gas sensor apparatus 1 are attached to the chamber 74. The volume of the chamber 74 used in the present experimental apparatus 70 is 360 cc (360 ml), and the diameter of the chamber 74 is 35 mm. The two-way valve 75 used in the present experimental apparatus 70 opens and closes the flow passage of the gas, and the period during which the flow passage is opened is controlled by the timer 76.

Figure 8A:
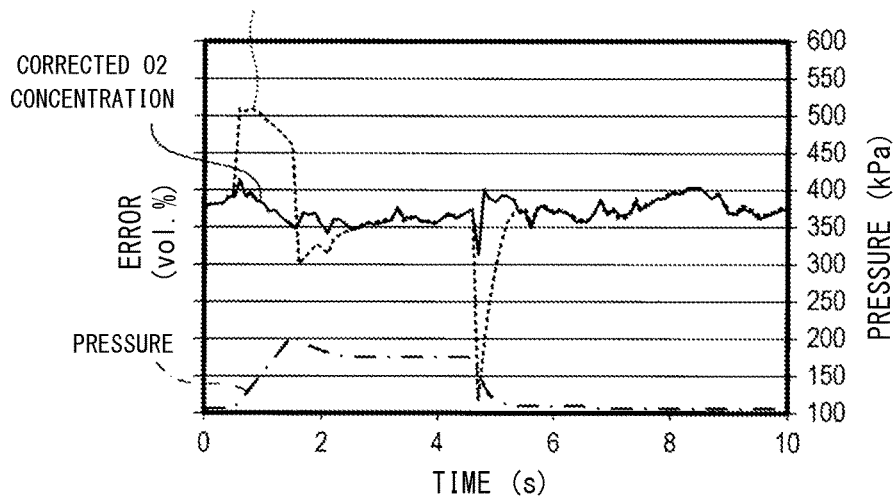
FIG. 8A is a graph showing a change in $O_2$ concentration with a change in gas pressure.

The experiment was performed at room temperature through the steps of setting the flow velocity of the gas to 40 L/min to 6 L/min, changing the pressure of the gas from 100 kPa to 200 kPa, and then returning the pressure to 100 kPa. FIG. 8A is a graph in which the horizontal axis represents time and the vertical axis represents the pressure of the gas and the error of the measured $O_2$ concentration.

It was found that, as shown in FIG. 8A, when the pressure of the gas increases from 100 kPa to 200 kPa, whereas the $O_2$ concentration before being corrected increases greatly due to the influence of the pressure change, the corrected $O_2$ concentration is not greatly influenced by the pressure change. Also, it is found that when the pressure of the gas decreases from 200 kPa to 100 kPa, whereas the $O_2$ concentration before being corrected decreases greatly due to the influence of the pressure change, the corrected $O_2$ concentration is not greatly influenced by the pressure change.

Figure 8B:
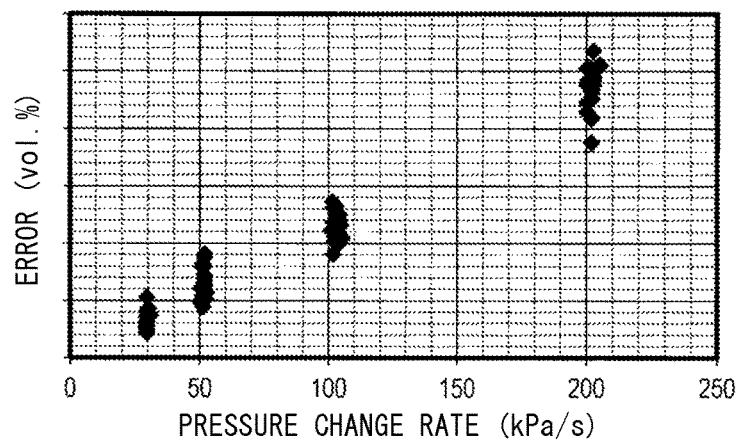
FIG. 8B is a graph showing the relation between gas pressure change rate and error of $O_2$ concentration.

FIG. 8B is a graph in which the horizontal axis represents pressure change rate and the vertical axis represents the error of the measured $O_2$ concentration. As shown in FIG. 8B, the error of the measured $O_2$ concentration increases with the pressure change rate (kPa/s) of the gas. The error exhibits a change which is approximately equal to a linear function whose variable is the pressure change rate. Therefore, in the present embodiment, the correction amount which is used to correct the $O_2$ concentration obtained in S10 is obtained by a method of multiplying the pressure change rate with the correction coefficient Cf. This correction coefficient Cf corresponds to the slope of the above-mentioned linear function. In other words, the correction coefficient Cf changes depending on the type of the oxygen sensor 10, and differs among individual oxygen sensors 10 of the same type.

According to the gas sensor apparatus 1 having the above-described configuration, when the pressure change rate exceeds the threshold Tha, the output value of the oxygen sensor 10 is corrected through use of a correction amount calculated based on the pressure change rate. In other words, in the case where the pressure changes dynamically, the output value of the oxygen sensor 10 is corrected through use of a correction amount corresponding to the degree of the dynamic change. Therefore, deterioration in the measurement accuracy of the $O_2$ concentration can be suppressed even when the pressure changes dynamically.

Meanwhile, when the pressure change rate is equal to or less than the threshold Tha, the correction of the output value of the oxygen sensor 10 performed using the correction amount calculated based on the pressure change rate is not performed. For example, in the case of a dynamic pressure change, such as the case where the pressure changes at a relatively high frequency, the correction of the output value of the oxygen sensor 10 is performed; and in the case of a static pressure change, such as the case where the pressure changes at a relatively low frequency, the correction of the output value of the oxygen sensor 10 is not performed. Therefore, deterioration in measurement accuracy can be suppressed even when the pressure changes dynamically.

Notably, in the above-described embodiment, the oxygen concentration before being corrected is calculated through use of Fick's law. However, the oxygen concentration may be calculated without the use of Fick's law, and no particular limitation is imposed on the method of calculating the oxygen concentration.

In the above-described embodiment, the current Ip which is the output value output from the oxygen sensor 10 is used as is for the calculation of the $O_2$ concentration. However, the $O_2$ concentration may be calculated through use of an output value obtained by removing the high frequency component contained in the current Ip by performing averaging processing.

Figure 9:
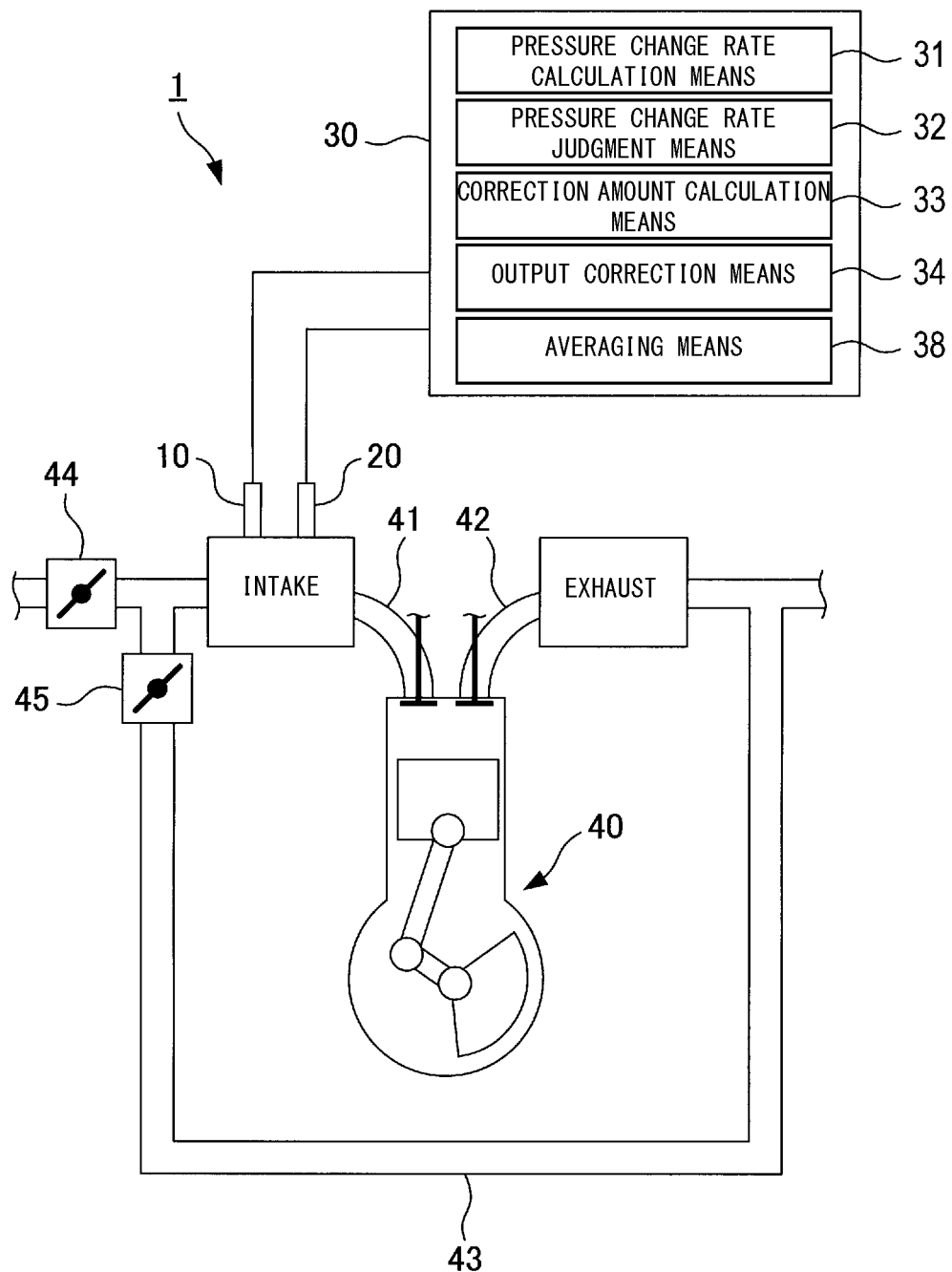
FIG. 9 is a schematic diagram showing another embodiment of the gas sensor apparatus of FIG. 1.

For example, as shown in FIG. 9, the ECU 30 may be configured to function as an averaging means 38 for removing the high frequency component. Alternatively, a circuit which functions as the averaging means 38 may be incorporated into the oxygen sensor 10 so that the oxygen sensor 10 outputs the current Ip from which the high frequency component has been removed. When the averaged current Ip is used, deterioration in the measurement accuracy of the $O_2$ concentration can be further suppressed.

Second Embodiment

Figure 10:
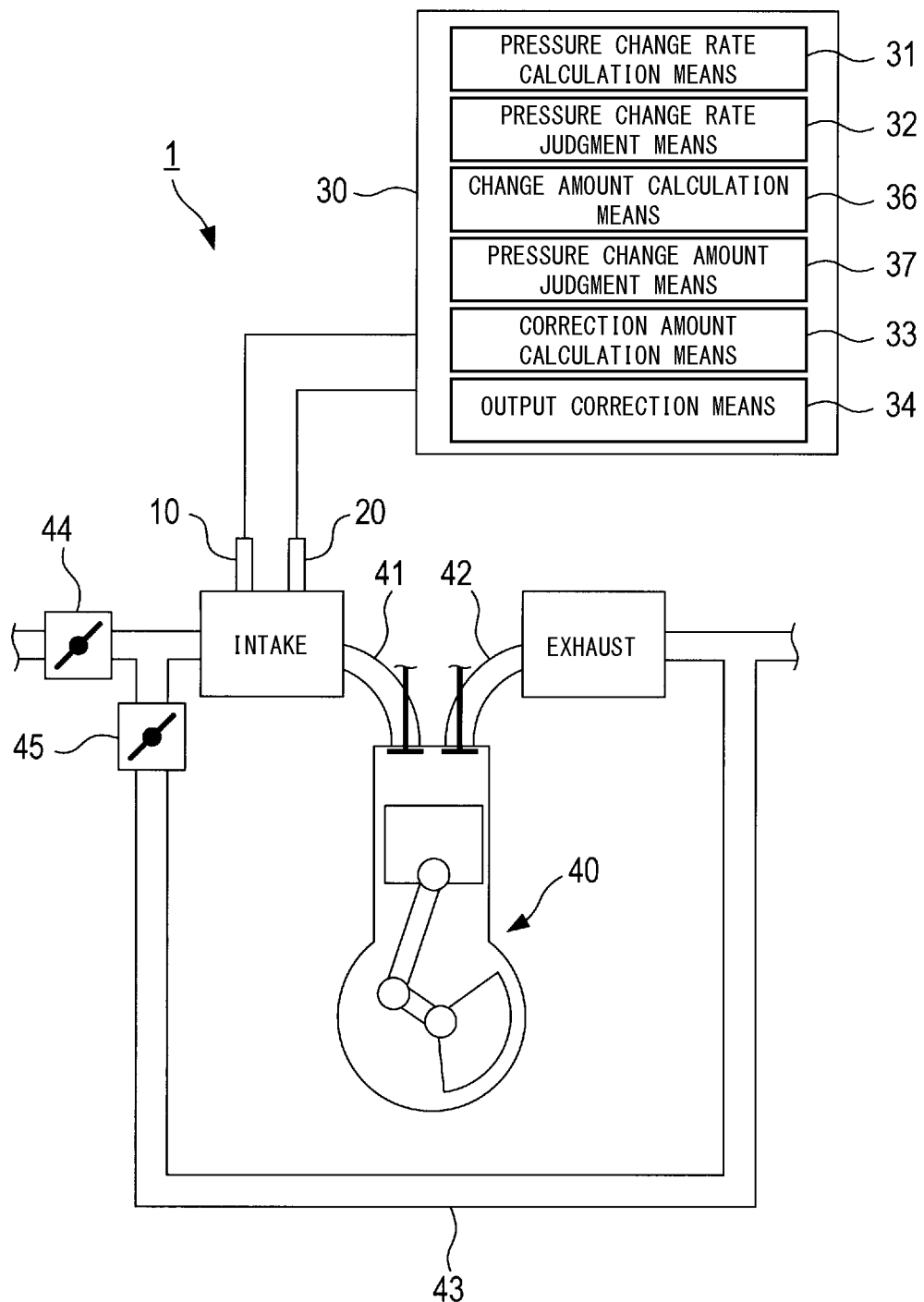
FIG. 10 is a schematic diagram showing the configuration of a gas sensor apparatus according to a second embodiment of the present invention.
Figure 11:
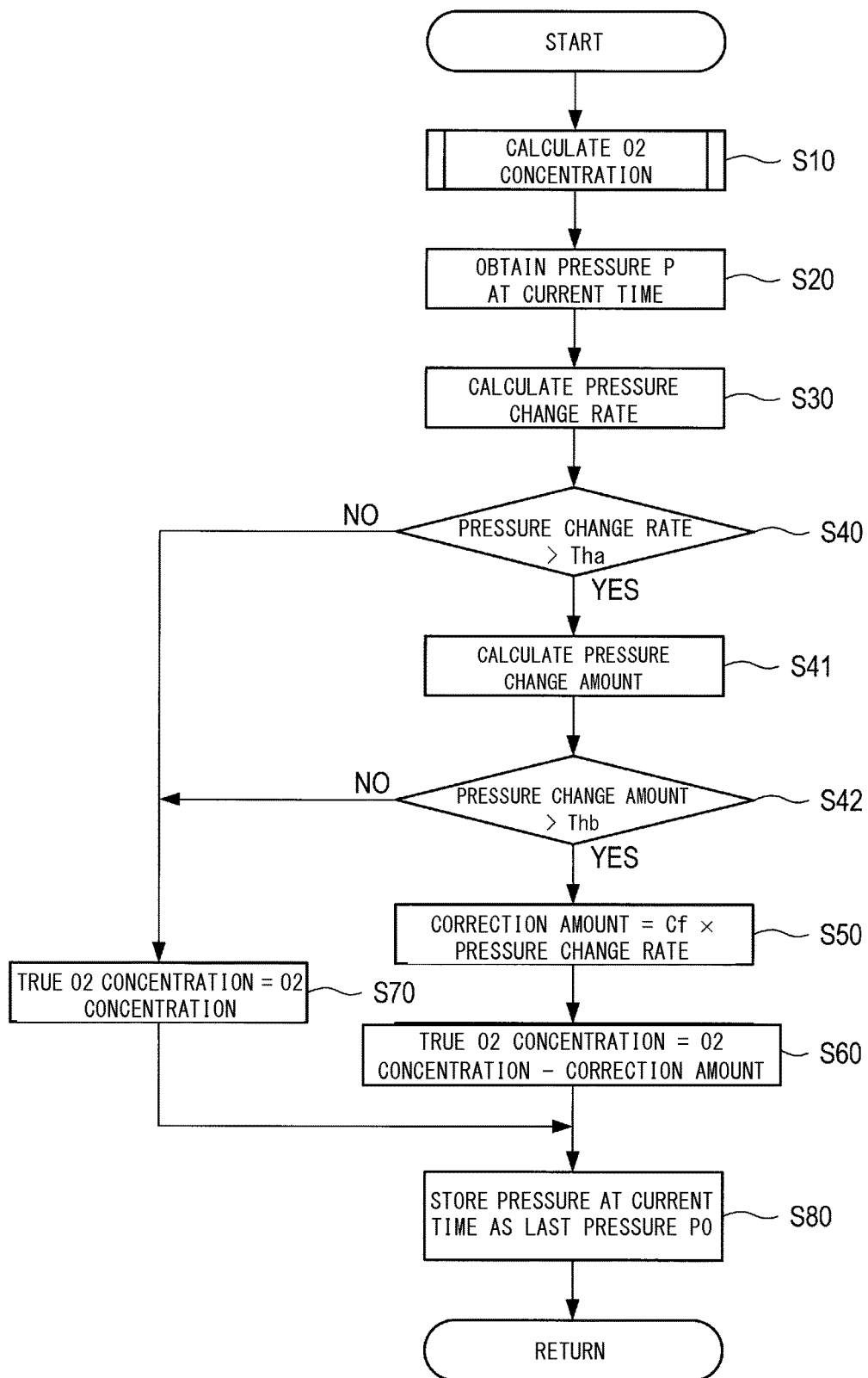
FIG. 11 is a flowchart describing an oxygen concentration correction method performed in the gas sensor apparatus of FIG. 10.

Next, a second embodiment of the present invention will be described with reference to FIGS. 10 and 11. Although the basic configuration of a gas sensor apparatus of the present embodiment is the same as the gas sensor apparatus of the first embodiment, the gas sensor apparatus of the present embodiment differs from the gas sensor apparatus of the first embodiment in the oxygen concentration calculation method. Only the oxygen concentration calculation method employed in the present embodiment will be described with reference to FIGS. 10 and 11, and descriptions of other structural elements, etc., are omitted.

The oxygen concentration calculation method in the gas sensor apparatus 1 of the present embodiment will be described with reference to the schematic diagram of FIG. 10 and the flowchart of FIG. 11. Notably, since the processing steps from S10 of calculating the oxygen concentration to S40 of comparing the pressure change rate and the threshold Tha are the same as those in the first embodiment, descriptions of these steps are omitted.

In the case where it is judged in S40 that the pressure change rate exceeds the threshold Tha (in the case of YES), change amount calculation means 36 provided in the ECU 30 performs processing of calculating a change amount of the pressure value (S41: a change amount calculation step). The pressure value change amount can be calculated by, for example, the following method. First, the last pressure value P0 obtained when the last $O_2$ concentration was calculated is obtained from the RAM of the output correction means 34 or the like, and the difference between the last pressure value P0 and the pressure value P at the time obtained in S20 is calculated whereby the change amount can be obtained. Notably, the method of calculating the pressure change rate is not limited to the above-described method, and various other methods can be used.

When the pressure value change amount is obtained, pressure change amount judgment means 37 provided in the ECU 30 performs processing of comparing the obtained pressure value change amount with a threshold Thb (a predetermined change amount) so as to judge whether or not the obtained pressure value change amount exceeds the threshold Thb (S42: a change amount judgment step).

In the case where it is judged that the pressure value change amount exceeds the threshold Thb (in the case of YES), the output correction means 34 performs computation processing of obtaining a correction amount (S50), and the output correction means 34 perform computation processing of obtaining an actual $O_2$ concentration (S60). Meanwhile, in the case where the pressure value change amount is judged that it is equal to or lower than the threshold Thb (in the case of NO), the output correction means 34 performs processing of the $O_2$ concentration obtained in S10 as the actual $O_2$ concentration (S70). Since the contents of the processing in subsequent steps are the same as those in the first embodiment, their description is omitted.

According to the gas sensor apparatus 1 having the above-described configuration, when the pressure value change amount exceeds the threshold Thb, the output value of the oxygen sensor 10 is corrected through use of a correction amount, whereby deterioration in the measurement accuracy of the $O_2$ concentration can be suppressed. For example, in the case of a static pressure change, such as the case where the pressure value change amount is equal to or less than the threshold Thb, the correction of the output value of the oxygen sensor 10 is not performed; and in the case of a dynamic pressure change, such as the case where the pressure value change amount exceeds the threshold Thb, the correction of the output value of the oxygen sensor 10 is performed. Therefore, deterioration in measurement accuracy can be suppressed even when the pressure changes dynamically.

In the above-described embodiment, the processing of calculating the pressure change rate (S30) and the processing of comparing the pressure change rate with the threshold Tha (S40) are performed prior to the processing of calculating the pressure value change amount (S41) and the processing of comparing the pressure value change amount with the threshold Thb (S42). However, the processing order is not limited to the above-described order, and the processing of calculating the pressure value change amount (S41) and the processing of comparing the pressure value change amount with the threshold Thb (S42) may be performed prior to the processing of calculating the pressure change rate (S30) and the processing of comparing the pressure change rate with the threshold Tha (S40).

The technical scope of the present invention is not limited to the above embodiments, and the embodiments may be modified in various ways without departing from the spirit of the invention. For example, the present invention is not limited to the above embodiments and may be applied to an appropriate combination of the above embodiments, and no particular limitation is imposed on the application of the invention.

The invention has been described in detail with reference to the above embodiments. However, the invention should not be construed as being limited thereto. It should further be apparent to those skilled in the art that various changes in form and detail of the invention as shown and described above may be made. It is intended that such changes be included within the spirit and scope of the claims appended hereto.

This application is based on Japanese Patent Application No. 2014-187834 filed Sep. 16, 2014, incorporated herein by reference in its entirety.

What is claimed is:

1. A gas sensor apparatus comprising:
a gas sensor which outputs an output value corresponding to the concentration of a specific gas component contained in a gas flowing through a flow passage provided in an internal combustion engine; and
a computation section which calculates a specific component concentration based on the output value output from the gas sensor and a pressure value representing the pressure of the gas,
the computation section comprising:
means for calculating a pressure change rate from a change in pressure per a predetermined time period;
means for judging whether or not the pressure change rate exceeds a predetermined rate;
means for calculating a provisional specific component concentration based on the output value output from the gas sensor and the pressure value representing the pressure of the gas;
means for calculating a correction amount for the provisional specific component concentration value based on the calculated pressure change rate when the pressure change rate is judged to have exceeded the predetermined rate; and means for correcting the provisional specific component concentration from the gas sensor using the correction amount calculated by the correction amount calculation means.

2. The gas sensor apparatus as claimed in claim 1, wherein the computation section further comprises means for calculating a change amount of the pressure value per the predetermined time period, and means for judging whether or not the change amount of the pressure value exceeds a predetermined change amount; and the correction amount calculation means calculates the correction amount for the output value based on the calculated pressure change rate when the pressure change rate judgment means judges that the pressure change rate has exceeded the predetermined rate and the pressure change amount judgment means judges that the change amount of the pressure value has exceeded the predetermined change amount.

3. The gas sensor apparatus as claimed in claim 1, further comprising a pressure sensor which measures the pressure of the gas and outputs a pressure raw value representing the measured pressure and averaging means for averaging the pressure raw value, wherein a value output from the averaging means is used as the pressure value.

4. A concentration measurement method performed using a gas sensor which outputs an output value corresponding to the concentration of a specific gas component contained in a gas flowing through a flow passage provided in an internal combustion engine, the method being adapted to calculate a specific component concentration based on the output value output from the gas sensor and a pressure value representing the pressure of the gas, the method comprising:

calculating a pressure change rate from a change amount of the pressure value per a predetermined time period;

calculating a provisional specific component concentration based on the output value output from the gas sensor and the pressure value representing the pressure of the gas;

judging whether or not the pressure change rate exceeds a predetermined rate;

calculating a correction amount for the provisional specific component concentration based on the calculated pressure change rate when the pressure change rate is judged to have exceeded the predetermined rate; and correcting the provisional specific component concentration from the gas sensor using the calculated correction amount.

5. The concentration measurement method performed using a gas sensor as claimed in claim 4, which further comprises:

calculating a change amount of the pressure value per the predetermined time period; and judging whether or not the change amount of the pressure value exceeds a predetermined change amount, wherein the correction amount calculation step calculates the correction amount for the output value based on the calculated pressure change rate when the pressure change rate is judged to have exceeded the predetermined rate and the change amount of the pressure value is judged to have exceeded the predetermined change amount.

* * * * *